United States Patent
Williamson, IV et al.

(10) Patent No.: US 10,314,585 B2
(45) Date of Patent: Jun. 11, 2019

(54) APPARATUS AND METHODS FOR OCCLUDING A HOLLOW ANATOMICAL STRUCTURE

(71) Applicants: Idx Medical, Ltd., Loveland, OH (US); The Cleveland Clinic Foundation, Cleveland, OH (US)

(72) Inventors: Warren P. Williamson, IV, Loveland, OH (US); Delos M. Cosgrove, III, Hunting Valley, OH (US)

(73) Assignees: IDx Medical, Ltd., Loveland, OH (US); The Cleveland Clinic Foundation, Cleveland, OH (US)

( * ) Notice: Subject to any disclaimer, the term of this patent is extended or adjusted under 35 U.S.C. 154(b) by 685 days.

(21) Appl. No.: 14/691,824

(22) Filed: Apr. 21, 2015

(65) Prior Publication Data
US 2015/0223813 A1 Aug. 13, 2015

Related U.S. Application Data

(63) Continuation of application No. 13/194,152, filed on Jul. 29, 2011, now Pat. No. 10,166,024, which is a continuation of application No. 11/994,725, filed as application No. PCT/US2006/027553 on Jul. 14, 2006, now abandoned.

(Continued)

(51) Int. Cl.
| | |
|---|---|
| *A61B 17/08* | (2006.01) |
| *A61B 17/122* | (2006.01) |
| *A61B 17/128* | (2006.01) |
| *A61B 17/10* | (2006.01) |
| *A61B 17/00* | (2006.01) |

(52) U.S. Cl.
CPC ............ *A61B 17/083* (2013.01); *A61B 17/10* (2013.01); *A61B 17/1227* (2013.01); *A61B 17/1285* (2013.01); *A61B 2017/00004* (2013.01)

(58) Field of Classification Search
CPC ... A61B 17/08; A61B 17/122; A61B 17/1227; A61B 17/1285; A61B 17/10; A61B 17/083
See application file for complete search history.

(56) References Cited

U.S. PATENT DOCUMENTS 2,371,978 A * 3/1945 Perham ................ A61B 17/085
24/530
5,026,379 A * 6/1991 Yoon ................ A61B 17/12013
606/141

(Continued)

FOREIGN PATENT DOCUMENTS

WO 2005060838 7/2005

*Primary Examiner* — Dianne Dornbusch
(74) *Attorney, Agent, or Firm* — Wood Herron & Evans LLP

(57) ABSTRACT

A clamp having at least first and second elongate clamping portions adapted to be placed on opposite sides of the hollow anatomical structure. The first and second elongate clamping portions respectively include ends coupled together with respective resilient urging members configured to urge at least one of the first and second elongate clamping portions toward the other of the first and second elongate clamping portions from an open position into a clamping position to occlude the hollow anatomical structure. The clamp includes tissue ingrowth structure on the clamping portions.

13 Claims, 11 Drawing Sheets

Related U.S. Application Data

(60) Provisional application No. 60/699,309, filed on Jul. 14, 2005.

(56) References Cited

U.S. PATENT DOCUMENTS

| | | | | |
|---|---|---|---|---|
| 5,217,473 | A * | 6/1993 | Yoon ................ | A61B 17/12013 606/141 |
| 6,960,218 | B2 * | 11/2005 | Rennich ............... | A61B 17/122 128/843 |
| 2005/0149068 | A1 * | 7/2005 | Williams ............. | A61B 17/122 606/151 |
| 2005/0149069 | A1 * | 7/2005 | Bertolero ................. | A61B 1/12 606/151 |
| 2005/0277959 | A1 * | 12/2005 | Cosgrove ............... | A61B 17/12 606/151 |
| 2006/0020271 | A1 * | 1/2006 | Stewart .............. | A61B 17/0057 606/139 |
| 2007/0213747 | A1 * | 9/2007 | Monassevitch .... | A61B 17/0643 606/151 |

* cited by examiner

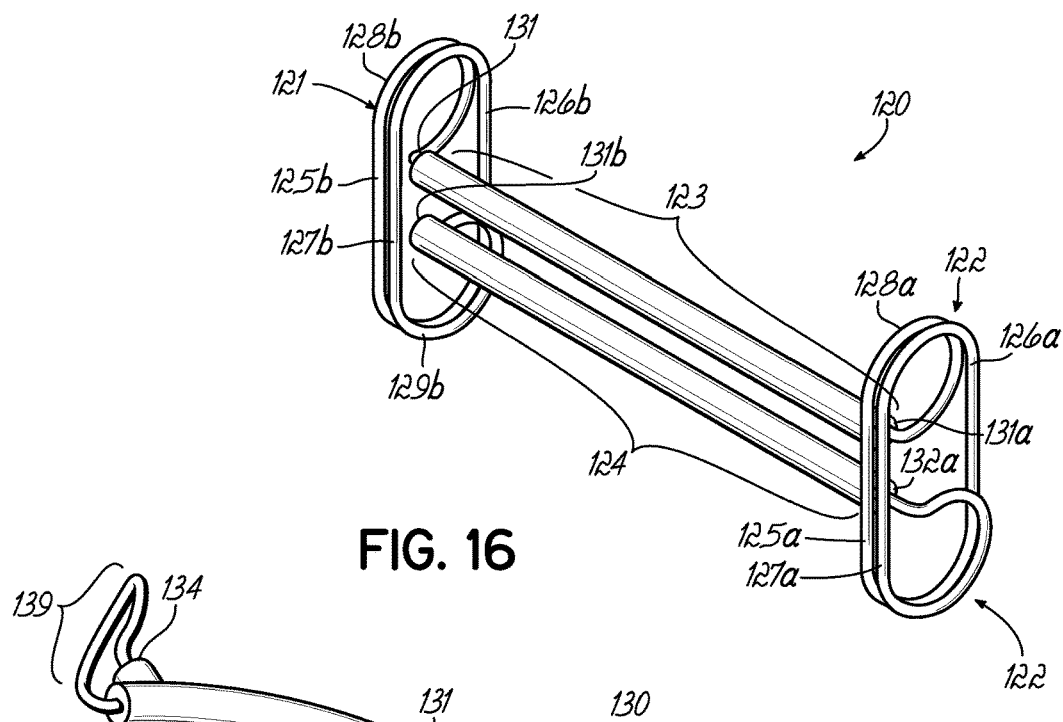
FIG. 16
FIG. 17
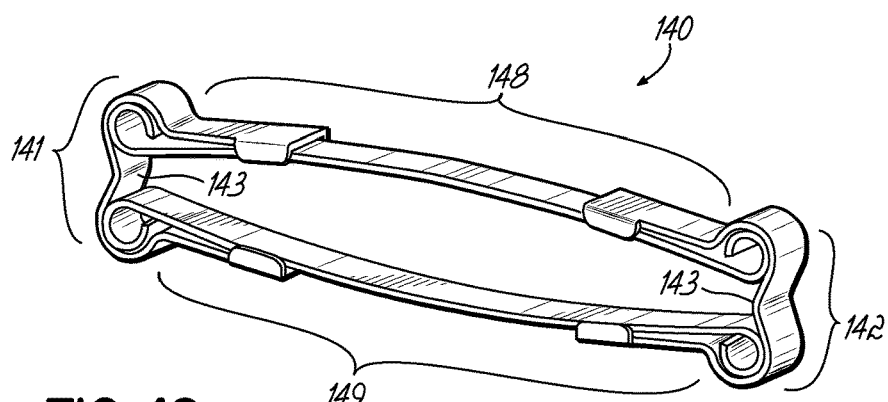
FIG. 18

APPARATUS AND METHODS FOR OCCLUDING A HOLLOW ANATOMICAL STRUCTURE

This application is a continuation of application Ser. No. 13/194,152, filed Jul. 29, 2011 which is a continuation of application Ser. No. 11/994,725, filed Jul. 8, 2008 (abandoned) which is a U.S. National Phase Application of PCT Serial No. PCT/US2006/027553, filed Jul. 14, 2006 (expired) which claims the benefit of U.S. Provisional Application Ser. No. 60/699,309 filed on Jul. 14, 2005 (expired), and generally relates to the subject matter disclosed and claimed in U.S. application Ser. No. 10/853,928, filed on May 26, 2004 (now U.S. Pat. No. 7,645,285). The disclosure of each of the above is hereby fully incorporated by reference herein.

FIELD OF THE INVENTION

The present invention relates generally to surgical methods and apparatus for occluding a hollow tissue structure, such as when occluding vessels, or pedunculated structures such as an appendix, gall bladder or appendages on the heart. More specifically, the present invention relates to a method and device for occluding the left atrial appendage of the heart in either an open surgical procedure or minimally invasive procedure.

BACKGROUND

Atrial fibrillation is a common cardiac rhythm disorder that affects more than two million people each year. Until relatively recently, atrial fibrillation was thought to be a nuisance arrhythmia with few consequences. However, recent medical research has uncovered some devastating complications including cardiomyopathy, congestive heart failure and stroke.

During atrial fibrillation the upper part of the heart beats (quivers) faster than the rest of the heart. This phenomenon is due to the generation of erratic or extra electrical signals which cause the top part of the heart to quiver rapidly and irregularly (fibrillate) as many as 300-600 times per minute. However, the entire heart does not beat that fast. The heart is a muscular pump divided into four chambers, with two atria on the top of the heart and two ventricles on the bottom portion of the heart. Normally, the heartbeat starts in the right atrium when a special group of cells sends an electrical signal. These cells are called the sinoatrial or SA node, sinus node or the heart's "pacemaker." The signal spreads throughout the atria and to the atrioventricular or AV node. The AV node connects to a group of fibers in the ventricles that conduct the electrical signal. The electrical impulse travels via these specialized fibers to all parts of the ventricles. The specialized fibers are also known as the His-Purkinje system. The electrical signal must follow this exact route for the heart to pump properly. Normally, the heart beats at 60-80 times per minute at rest. This number represents the contractions of the lower heart or ventricles. During atrial fibrillation, electrical signals from other parts of the heart disrupt the heart's normal rhythm and cause the atria to quiver or beat too fast. However, only a small number of these atrial beats make it through the AV node, which acts like a gate to the ventricles. This is fortunate, because a rapid ventricular heartbeat would be much more dangerous and potentially fatal. However, some atrial fibrillation does make it through the AV node making the heart beat faster than normal. An atrial fibrillation attack is usually not life threatening. The most significant danger is stroke.

Blood usually moves completely through the chambers of the heart. During atrial fibrillation, the heart is not pumping normally or efficiently. The blood begins to pool in the atria and this stagnation of blood can cause the blood to thicken and form clots. These clots are then ejected out of the heart and into the bloodstream where they can lodge in the brain causing a stroke. Atrial fibrillation can make stroke five times more likely than in the general population. When the heart experiences atrial fibrillation there may not be enough blood pumping to the brain or other organs. This can cause dizziness, shortness of breath or organ failure. Untreated atrial fibrillation will also weaken the heart due to phenomenon known as remodeling. The heart, like the rest of the body, adapts to changes. The fast abnormal rhythm in the atria causes electrical changes, and this can enlarge the heart.

There are three major objectives in the treatment of atrial fibrillation: the restoration of normal sinuous rhythm, control of ventricular rate during atrial fibrillation, and the prevention of blood clot formation. Some methods of treatment for atrial fibrillation include pharmacological therapy, pacemakers, and surgery.

For the prevention of blood clots, research has demonstrated that the anticoagulant warfarin (e.g., Coumadin®) is effective in reducing the risk of blood clot formation and stroke but it does not totally eliminate the risk. An anticoagulant such as warfarin interferes with the body's natural clotting mechanism. The dosage of warfarin is highly individualized and must be carefully monitored with blood tests to ensure safety. While this pharmacological treatment may significantly reduce the risk of stroke, it also increases the risk of bleeding and may be inappropriate for many atrial fibrillation patients.

As an alternative to pharmacological therapy, there are a few surgical procedures that isolate the left atrial appendage from the blood's circulatory system. The left atrial appendage is a small hollow extension (i.e., a pedunculated structure) formed off the lateral wall of the left atrium. It has been referred to as a small "windsock" like structure or a small, flat hollow finger-like protrusion. The left atrial appendage usually contracts with the rest of the left atrium during normal heart function thereby continually moving blood throughout the hollow extension. During atrial fibrillation, the left atrial appendage often fails to contract thereby allowing the blood to pool inside the appendage, becoming stagnated. As a result, the blood becomes thicker and thrombus or clot formation may occur. These clots can be slowly ejected from the left atrial appendage into the left atrium and left ventricle, and then released into the bloodstream thereby becoming an obstruction in the brain or other vascular structures. For this reason, it is advantageous to prevent these clots from forming and being dislodged into the bloodstream. One method of preventing the occurrence of clots is to occlude the appendage thus preventing blood from entering and forming clots. This also prevents clots already formed in the appendage from escaping into the bloodstream. Normally, the occlusion of the left atrial appendage is performed in conjunction with other procedures such as a mitral valve replacement or coronary artery bypass procedure and not as the sole reason for the procedure.

There are several different methods being used today to occlude the left atrial appendage. One method is percutaneous left atrial appendage transcatheter occlusion. A small occlusion device is deployed from a venous access catheter into the left atrium and blocks the opening into the atrial appendage. In order to access the left atrium from the vena cava's right atrium, the surgeon must go through the atrial wall. Many surgeons are uncomfortable with making an opening in this wall without being able to repair it at the end of the procedure. There are also issues of placing an occlusion device inside the heart. If the occlusion device becomes detached within the heart, the result may be fatal.

Another method of occlusion is placing a loop around the left atrial appendage and cinching it down in a manner similar to a garrote. When trying to place a flaccid loop around an irregular pedunculated structure, it can be difficult to make certain the loop is positioned at the base of the appendage. When cinching the loop, it is very easy to over tighten the loop, and this can result in severing the delicate atrial appendage. Even a partial tear can create problems, including the initial problem of gaining access to repair the tear. This method of occlusion may not always seal the opening between the appendage interior and the atrium. That is, there may still be a partial opening due to the way the appendage wall collapses during cinching of the loop. Such a partial opening could still allow some flow into and out of the atrial appendage, leading to the problems mentioned above. In addition, transforming the relatively flat structure of the appendage onto a round hard mass, as does a cinching method, could lead to other problems.

Another method of occlusion is to place a linear surgical stapler at the base of the appendage and a left atrial wall and staple the appendage closed. Due to the limited access, the ability to visualize the entire atrial appendage while placing the stapler in the correct location can be a problem. It is very difficult to make certain the staple line makes a complete occlusion of the appendage. Again, a partial occlusion of the appendage can still result in the formation and dislodgement of clots.

For the aforementioned reasons, it would be desirable to provide improved methods and devices to reliably occlude hollow anatomical structures, including but not limited to the left atrial appendage of the heart, completely and safely. Such methods may be performed during an open-heart surgical procedure such as a valve replacement or coronary artery bypass. It would also be desirable to provide methods and devices that may be used in minimally invasive or less invasive procedures while the heart is beating without placing the patient on a heart-lung bypass machine. A less invasive device may allow, for example, access through either an intercostal space between the ribs or a supra and/or sub-xiphoid approach to gain access to the left atrial appendage. Such devices may allow complete visualization of the left atrial appendage for the surgeon and permit minor placement adjustments to be made before permanent installation is made. The devices would also allow complete occlusion of the left atrial appendage, eliminating the risk of clots forming in the appendage, traveling throughout the bloodstream, and possibly lodging in the brain causing a stroke.

SUMMARY

In one aspect, the present invention is directed to a device for occluding a hollow anatomical structure, with the device including a clamp having at least first and second elongate clamping portions adapted to be placed on opposite sides of the hollow anatomical structure. The first and second elongate clamping portions respectively have ends coupled together with respective resilient urging members configured to urge at least one of the first and second elongate clamping portions toward the other of the first and second elongate clamping portions from an open position into a clamping position to occlude the hollow anatomical structure. The clamp comprises an annular shape configured to surround the hollow anatomical structure in the open position and a flattened shape in the clamping position configured to occlude the hollow interior of the hollow anatomical structure.

The resilient urging members may normally spring bias at least one of the first and second elongate clamping portions toward the other of the elongate clamping portions. For example, any number of designs may be used for the resilient urging members, including various types of separate or integrally formed spring elements on the clamp. One or more generally U-shaped wire sections may be used at opposite ends, for example. The clamping portions may have tissue engaging surfaces adapted to promote tissue ingrowth, such as a tissue engaging surface having pores with diameters sized from about 200 to about 400 microns. The surface may, for example, comprise a surgical grade fabric. The tissue contacting surface may be a surface that prevents line contact with the hollow anatomical structure thereby spreading a load force exerted by the first and second elongate clamping portions on the tissue. The first and second elongate clamping portions may have complementary shapes in cross section such that the complementary shapes fit together in the clamping position. This may be achieved through either a preformed shape in the elongate clamping portions, or by forming one or both the elongate clamping portions, or at least one or more outer layers thereof, out of a material that is deformable under load. Any other features in the above incorporated patent application may also be incorporated into the device as further disclosed herein.

In one aspect, the first and second elongate clamping portions and the resilient urging members may be formed from at least one wire member. The wire member may be formed from a material having superelastic properties, such as a nickel-titanium alloy, or from other materials having suitable physical characteristics for achieving the clamping function. Rigid and/or resilient tubular members may be used to cover the wire member respectively on the first and second elongate clamping portions. Such first and second tubular shaped members can, for example, provide more effective load spreading by increasing the diameter of the wire member.

In another aspect of the invention, tissue blocking members are positioned at opposite ends of the elongate clamping portions and prevent outward egress of clamped tissue beyond the respective ends of the elongate clamping portions.

In another aspect of the invention, the first and second elongate clamping portions may comprise elongate generally parallel members capable of reorienting into a nonparallel relationship in the clamping position. For example, the generally parallel members may reorient into a nonparallel relationship which converges toward one end of the clamp or the other end of the clamp.

Apparatus according to the invention may include a clamp with any of the features discussed above, and a clamp delivery and actuation device including first and second jaws for carrying and deploying the clamp onto the hollow anatomical structure.

Methods according to the invention are also contemplated and generally include use of the device or apparatus as described above including any of the desired features discussed herein.

BRIEF DESCRIPTION OF THE DRAWINGS

FIG. 16 shows an alternate embodiment of the clamp of FIG. 12 having multiple-turn urging members.

FIG. 17 shows an alternate embodiment of a clamp in which the ends of the clamping portions overlap each other.

FIG. 18 shows an alternate embodiment of the clamp of FIG. 15 having a greater space between the clamping portions in the clamping portions' end sections.

DETAILED DESCRIPTION OF THE ILLUSTRATIVE EMBODIMENTS

Figure 1A:
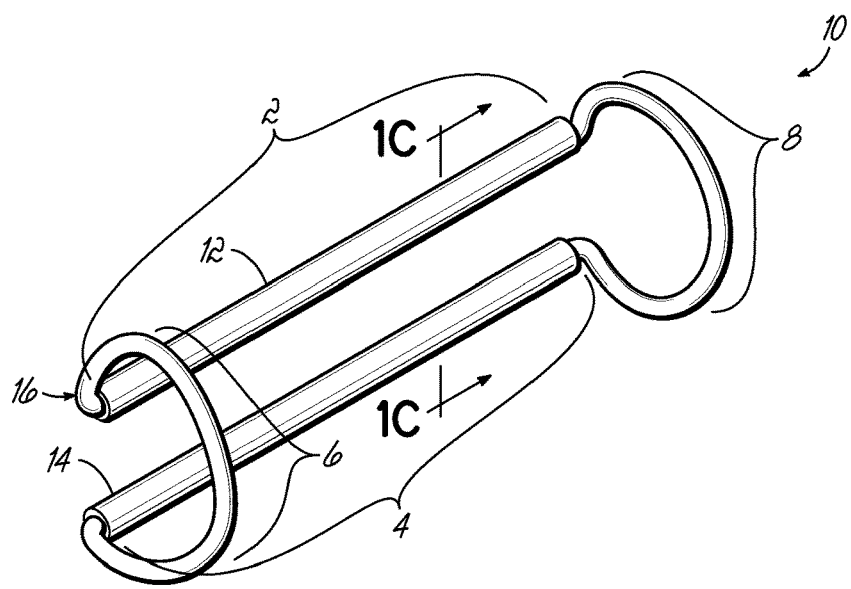
FIG. 1A is a perspective view of a first embodiment of a clamp in an open position.
Figure 1B:
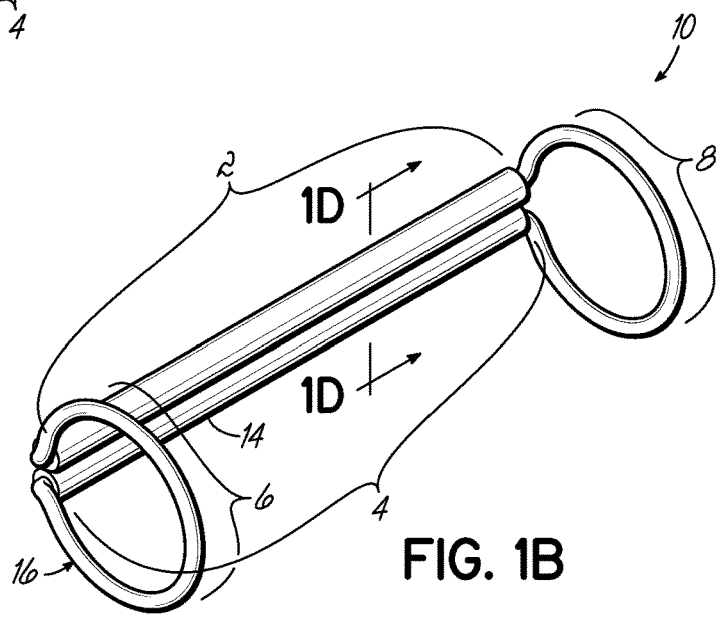
FIG. 1B shows a perspective view of the clamp in a closed position.
Figure 1C:
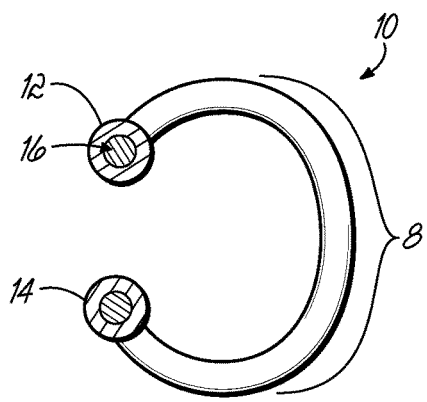
FIG. 1C is a cross-sectional view of the clamp of FIG. 1A in its open configuration, showing the wire member, rigid tubular members, and the urging members.

FIGS. 1A and 1C show one embodiment of a left atrial appendage occlusion clamp 10 in an open position with spaced apart rigid clamping portions 2, 4 and resilient or elastic urging members 6, 8 at opposite ends of each clamping portion 2, 4. Clamping portions 2, 4 may be tubular, and both clamping portions 2, 4 may be at least substantially parallel to each other when at rest, i.e., when they are not being used to clamp tissue. Clamping portions 2, 4 may also be of substantially equal length or of different length, and each may be of larger outer diameter than the wire that may be used to form each of the urging members 6, 8. In this regard, the wire forming urging members 6, 8 can extend through the hollow interiors of the clamping portions 2, 4. In this illustrative example, the urging members 6, 8 are each shaped as a loop. The planes defined by the looped configuration of each of the urging members 6, 8 may be substantially parallel to each other and, in turn, substantially perpendicular to each of the clamping portions 2, 4. Of course, other angular orientations are possible as well.

Figure 1D:
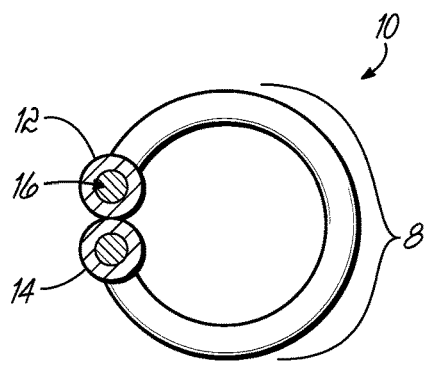
FIG. 1D is a cross-sectional view of the clamp of FIG. 1B in its closed configuration, showing the wire member, rigid tubular members, and the urging members.
Figure 3:
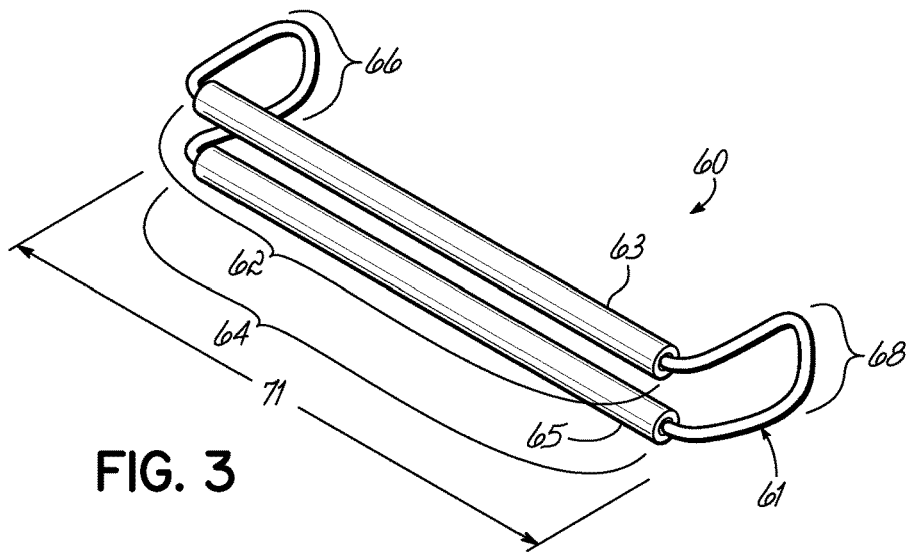
FIG. 3 is a perspective view of the first stage of assembly of an alternate embodiment of a clamp, showing a wire member surrounded by rigid tubular members.
Figure 4:
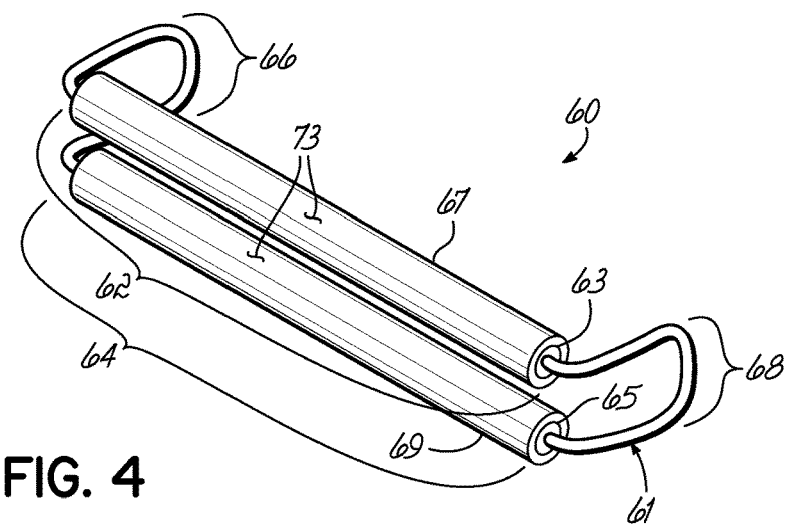
FIG. 4 is a perspective view of the second stage of assembly of the clamp of FIG. 3, in which platens have been added over the rigid tubular members.
Figure 5:
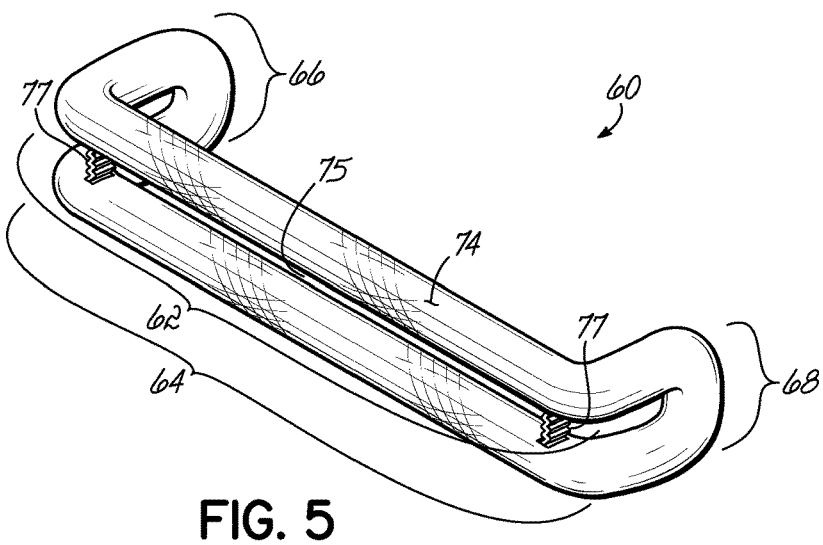
FIG. 5 is a perspective view of the clamp of FIGS. 3 and 4, once an outer fabric covering has been disposed over the entire surface of the clamp.

FIGS. 1B and 1D show the same clamp 10 of FIGS. 1A and 1C with the clamping portions 2, 4 in their normally biased together positions. Contact between the clamping portions 2, 4 may occur initially along their entire parallel lengths as shown. Of course, when clamping portions 2, 4 are covered in fabric or other material as later described, contact may occur between the fabric or other material instead. In FIGS. 1A-1D, only the structure and relative positions of the rigid members 2, 4 and urging members 6, 8 are shown. The final assembly is depicted in FIGS. 3, 4 and 5 which, although describing a slightly different embodiment, show the general steps in the construction of each embodiment. The clamping portions 2, 4 may be made from rigid tubes 12, 14 of a rigid metal such as titanium disposed over a wire member 16. In this embodiment, titanium is used for its compatibility with MRI imaging, its biocompatibility and its galvanic compatibility with the wire member 16 when the wire member 16 is formed from superelastic materials such as a nickel titanium alloy. This embodiment and the other embodiments disclosed herein may use a superelastic material such as a nickel titanium alloy to form the urging members 6, 8. Superelastic properties will allow the material to be greatly extended to open the clamping portions 6, 8 of the clamp 10 without permanently deforming the material. These superelastic materials can also be compatible with MRI imaging and easily tolerated as an implant material in the body. The rigid tubular members 12, 14 of this embodiment are mechanically fastened to the underlying wire member 16 preferably by mechanically swaging the titanium tubes 12, 14 to the wire members 16. Although a single, continuous wire member is shown directed through both clamping portions 2, 4 and urging members 6, 8, the clamp 10 of this embodiment may also be made with two or more wires, or with any other suitable components.

Figure 2:
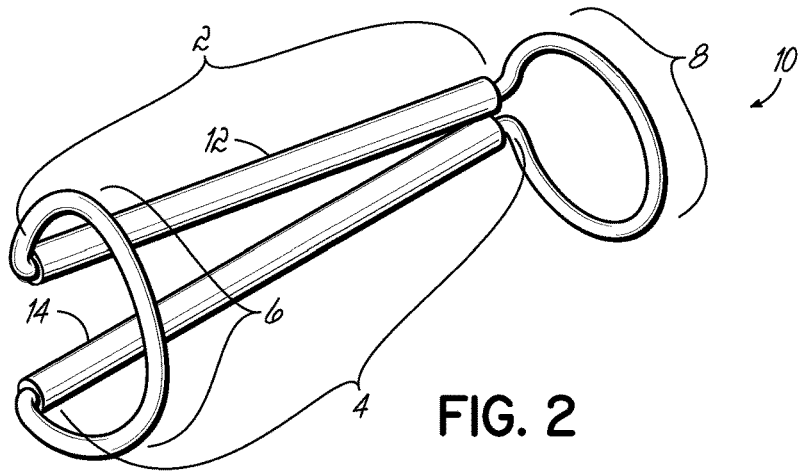
FIG. 2 shows a perspective view of the occlusion clamp of FIGS. 1A-1D and showing the ability to close in a non-parallel fashion.

As shown in FIG. 2, in addition to being able to close on tissue or anatomical structure in a parallel fashion, the clamp 10 can also apply force to the anatomical structure in a nonparallel clamping fashion. This allows the clamp 10 to accommodate non-uniform tissue thickness over the length of the clamping portions 2, 4. In addition, with separate urging members 6, 8 at opposite ends of the clamping portions 2, 4 the nonparallel clamping can originate from either side of the clamp 10. The non-parallel clamping feature of this embodiment allows the clamp 10 to accommodate a wide range of hollow anatomical structures with varying wall thicknesses throughout its length and breadth. For example, some anatomical structures such as atrial appendages 40 (FIG. 9) of the heart 50 have internal structures called trabeculae, which are non-uniform and very often cause variable thicknesses across one or more of their dimensions. Nonuniform clamping, therefore, can be advantageous in this application for this reason or for other reasons.

FIG. 3 shows an alternate embodiment of a clamp 60 including two urging members 66, 68 shaped to resemble a letter "U" instead of the more circular loop configuration of the embodiment of FIGS. 1A-1D. As is the case with the first clamp 10, the U-shaped urging members 66, 68 of clamp 60 may also lie in planes generally parallel to each other and perpendicular to the axes of the clamping portions 62, 64. A potential use of the embodiment of FIG. 3 may lie in the lesser force exerted by U-shape urging members 66, 68 on the clamping portions 62, 64 with respect to the force exerted by the loop-shape urging members 6, 8 of clamp 10 in FIGS. 1A-1D, making it more suitable for clamping of anatomical structures not requiring a relatively high clamping force. The U-shape configuration of the urging members 66, 68 generally requires less space in the direction perpendicular to the axes of the clamping portions 62, 64. FIG. 3 shows a first stage of assembly of the clamp 60, where the rigid tubular members 63, 65 are joined with the superelastic wire member 61. In this embodiment, mechanical swaging is used to join the tubular members 63, 65 to the wire 61. However, adhesives or laser welding or other methods of attachment could be easily used instead. Similarly, it will be appreciated that rigid tubular members 63, 65 may not necessarily need to be bonded to wire member 61 at all. One may rely, for example, on designing the rigid tubular members 63, 65 so that their inside diameters simply closely fit over the wire 61. In addition, the rigid tubular members 63, 65 could take on many different cross sectional shapes. Cross-sectional shapes such as ovals, triangles or rectangles with rounded edges could be preferable and may eliminate the addition of the load spreading platens 67, 69 shown in FIG. 4, as these alternate shapes may provide a larger area of contact against the anatomical structure to be engaged by the clamp 50. Since different anatomical structures greatly vary from subject to subject, it is advantageous to have a manufacturing method in which the length 71 of the clamp 60 can be easily varied. By cutting rigid members 63, 65 to various different lengths, different size assemblies can be configured.

FIG. 4 shows the next step in the assembly of the clamp. Load spreading platens 67, 69 made of plastic or other biocompatible material such as urethane, may be slipped over the titanium or other suitable material tubing that forms rigid tubular members 63, 65, to provide a resilient surface 73 to spread the load out onto a larger surface area, thereby preventing point source loading of the tissue which might otherwise result in cutting of the tissue before it has had a chance to become internally fused. The platens 67, 69 can be assembled and applied over the rigid tubular members 63, 65 prior to the swaging step or platens 67, 69 can alternatively be manufactured in such a way so as to have a longitudinal split which allows the material to be opened and forced onto the rigid tubular members 63, 65.

FIG. 5 shows the clamp 60 after a fabric cover material 74 made of material such as polyester has been sewn around the clamping portions 62, 64 and urging members 66, 68. It will be appreciated that this material or any other similar materials may be used as a full or partial covering in any of the disclosed embodiments. Such a material is preferably suitable to engage the tissue of the anatomical structure being clamped as well as that of surrounding areas. Preferably, the material 74 is circular warp knit fabric tube, with a diameter of approximately 4 to 5 mm and made from a combination of 4/100, 2/100 and 1/100 textured polyester. The material 74 may also be heat-treated to cause a velour effect. The fabric or other material 74 is furthermore sewn or otherwise applied over the urging members 66, 68. In addition, fabric pieces 77 may be attached at opposite respective ends of clamping portions 62, 64 to prevent any part of the engaged anatomical structure from escaping the annular occlusion area 75 (FIG. 9) between the clamping portions 62, 64. In other words, fabric pieces 77 act as tissue blocking members or dams at opposite ends of the clamp. This or another tissue blocking feature may also be implemented into any other embodiment. This is desirable as it minimizes the probability of unintentionally leaving any part of the engaged anatomical structure unclamped. The material 77, like material 74, can also promote tissue ingrowth.

Figure 6A:
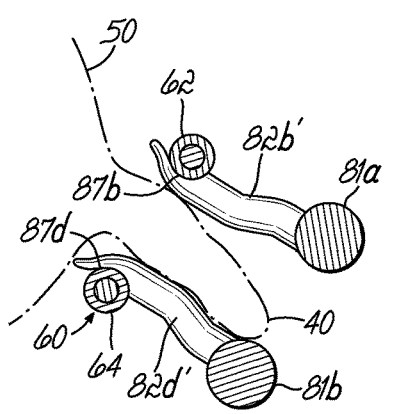
FIG. 6A is a cross sectional view taken generally along line 6A-6A of FIG. 6, but illustrating an alternative embodiment of the spreader legs in an open or spread position.
Figure 6B:
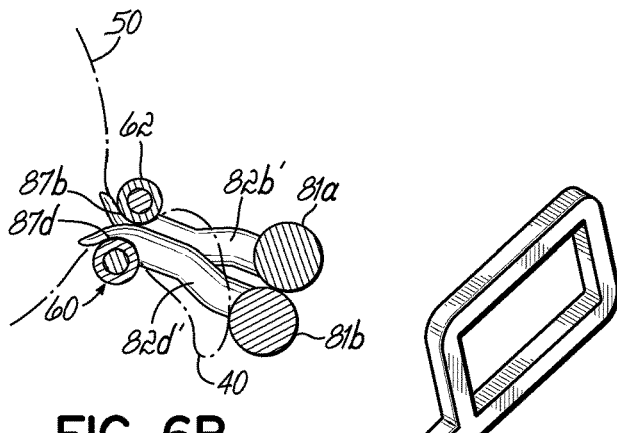
FIG. 6B is a view similar to FIG. 6A, but illustrating the tool in a closed or clamping position.
Figure 6:
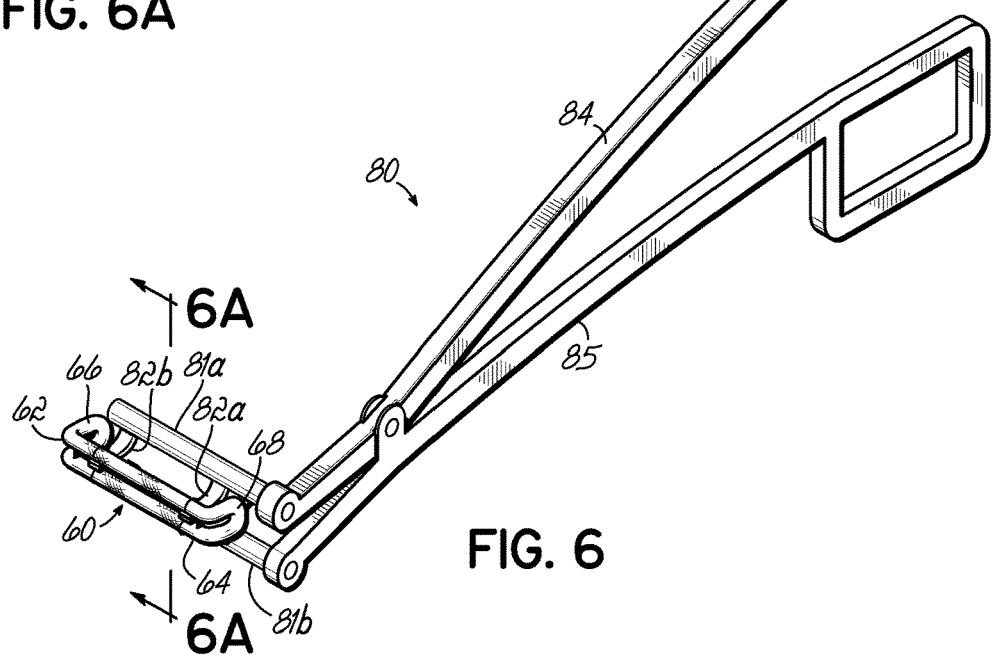
FIG. 6 is a perspective view of a deployment tool used to apply the clamp of FIG. 5, with the clamp shown in the closed position.
Figure 7:
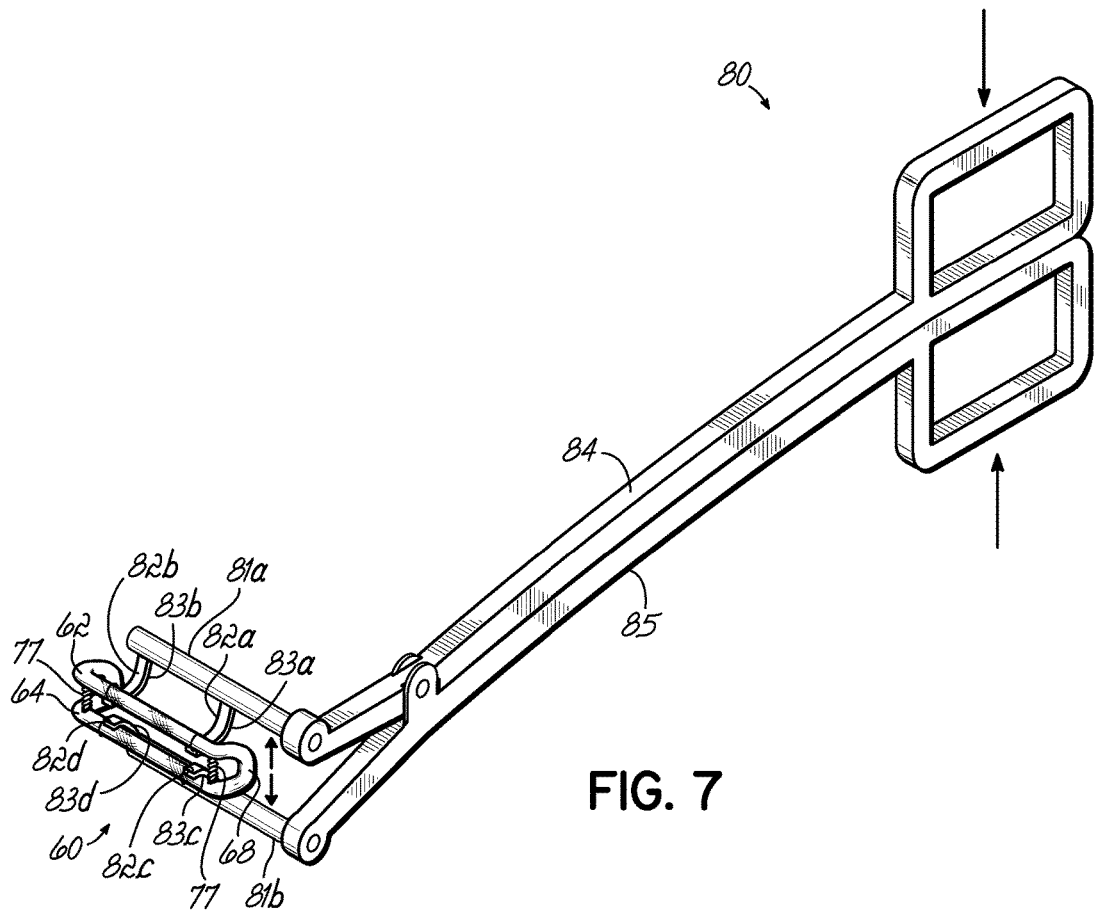
FIG. 7 is a perspective view of the deployment tool and clamp of FIG. 5 with the clamp shown in the open position.

FIGS. 6 and 7 show a deployment tool 80 for opening the clamp 60 sufficiently to allow an appendage 40 or other tissue or anatomical structure to be placed between the clamping portions 62, 64 and then release the clamp 60 from the deployment tool 80 to allow the normal closing force of the clamp 60 to be deployed onto the appendage 40 to be treated. The deployment tool 80 of this embodiment is a scissor type arrangement with transverse support members 81a, 81b having spreader legs or jaws 82a, 82b, 82c, 82d. Each arm 84, 85 of the deployment tool 80 has two spreader legs 82a, 82b, 82c, 82d. Support members 81a, 81b are connected to handles 84, 85 for operation as will be apparent from reviewing FIGS. 6 and 7. The spreader legs 82a, 82b, 82c, 82d have curved receiver portions 83a, 83b, 83c, 83d at each distal end to engage the clamp 60. The receiver portions engage the clamp in opposing directions generally parallel to a plane containing both clamping portions 62, 64. The receiver portions 83a, 83b, 83c, 83d are generally concave, allowing the clamping portions 62, 64 to be more securely engaged in the extending spreader legs 82a, 82b, 82c, 82d. Alternative embodiments may consist of other methods and deployment tool portions suitable to securely but releasably hold the clamping portions 62, 64 of the clamp 60, thus preventing the clamp 60 from being released prior to proper deployment onto the treated appendage 40 or other anatomical structure. These may include flat or curved spreader legs 82a, 82b, 82c, 82d, and may also include, for example, sutures 81a, 81b, 81c, 81d (see FIGS. 8-10) or other manners of releasably joining the clamp 60 to the tool 80.

Figure 8:
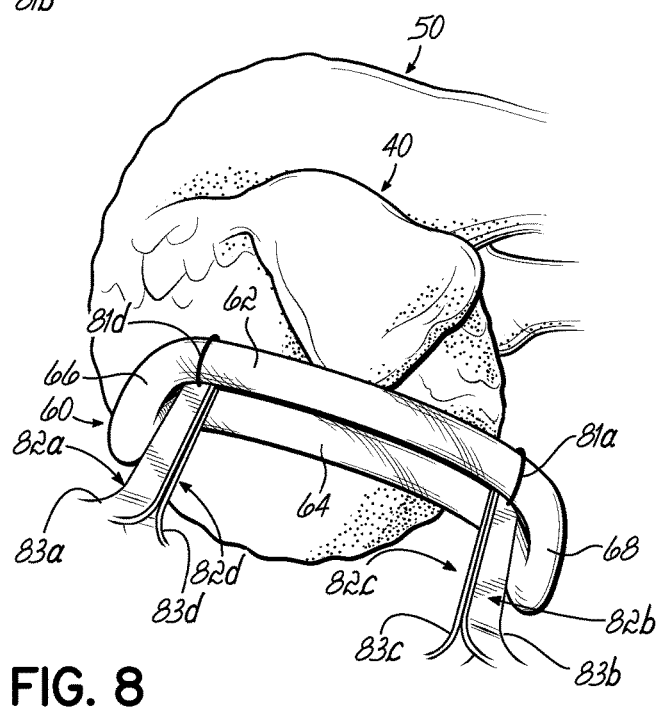
FIG. 8 shows the deployment tool and clamp of FIG. 5, with the tool holding the clamp in its closed position.
Figure 9:
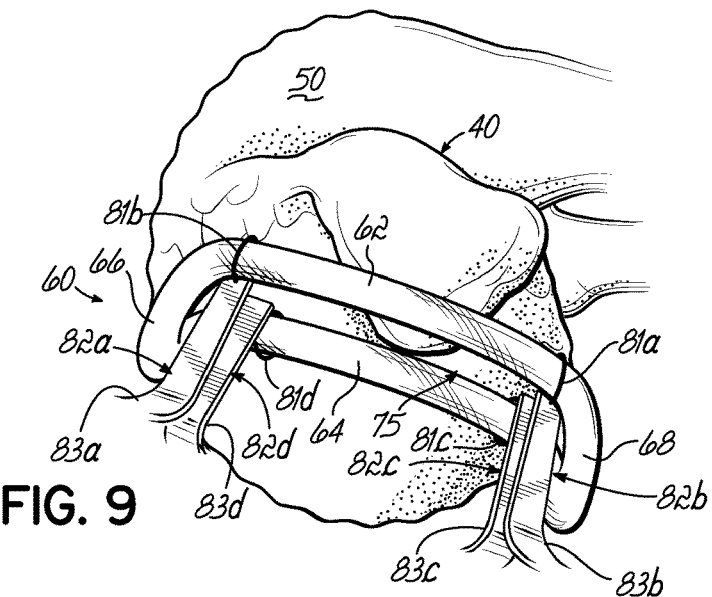
FIG. 9 shows the deployment tool and clamp of FIG. 5, with the tool holding the clamp in a partially open position immediately prior to deployment.
Figure 10:
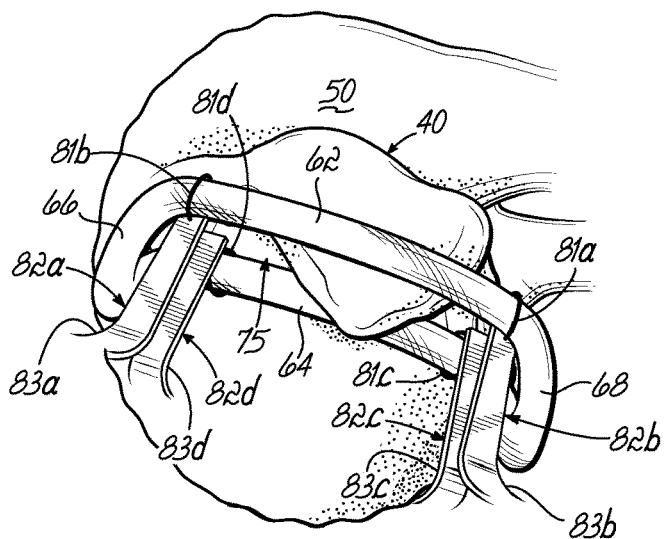
FIG. 10 shows the deployment tool and clamp of FIG. 5, with the tool deploying the clamp over an appendage.

FIGS. 6A and 6B illustrate cross sectional views of clamp 60 held on legs 82b', 82d'. Identical numerals in FIGS. 6A and 6B represent like elements of structure as compared to the embodiment of FIG. 6 and, therefore, further description of such elements is not necessary. Like reference numerals with prime (') marks are slightly modified elements as between the embodiments, and as described further herein. It will be appreciated that only two of four legs are shown in FIGS. 6A and 6B, however, the remaining two legs may be identically designed. Legs 82b', 82d' have recesses 87b, 87d for complementing the shape of the clamping portions 62, 64 held therein. This shape retains the clamp on the legs 82', 82d' without any other retaining structure or element being necessitated, such as one or more severable sutures 81a, 81b, 81c, 81d as shown in FIGS. 8-10. In this manner, after the legs 82b', 82d' are moved from the open or spread position shown in FIG. 6A to the closed or clamping position shown in FIG. 6B to, for example, apply the clamp 60 to the left atrial appendage 40, the legs 82b', 82d' may simply be slipped out from between clamping portions 62, 64.

FIG. 8 shows the deployment tool 80 of FIGS. 6 and 7 with the clamp 60 engaged in the spreader legs 82a, 82b, 82c, 82d but in its closed position. The clamp 60 may be moved into the general anatomical area where the appendage 40 or other structure is located while the clamp 60 is in a closed position. This can allow for smaller entry wounds and/or easier maneuvering to the clamping site. The clamp 60 is releasably held onto legs 82a, 82b, 82c, 82d with respective severable sutures 81a, 81b, 81c, 81d. The ability of the deployment tool 80 to securely but releasably hold the clamp 60 therefore allows for this type of pre-deployment movement to be effected without concern for the possibility of premature or unwanted separation of the clamp 60 from the tool 80.

FIG. 9 shows a deployment tool 80 partially opening the clamp 60, applying a force sufficient to overcome the bias of the urging members 66, 68 of the clamp 60 to close the clamping portions 62, 64 towards each other. The tool 80 directs the clamp in a direction generally oriented so that the appendage 40 will be approximately in the region of the annular opening 75 of the clamp 60. The appendage 40 is placed through the opening 75 of the clamp 60 between the two urging members 66, 68. At the point of the procedure shown in FIG. 9, the deployment tool 80 securely continues to hold the clamp 60 by the clamping portions 62, 64, in one of the manners described above.

FIG. 10 shows the appendage 40 of FIGS. 8 and 9 being positioned in the clamp 60. Note that the spreader legs 82a, 82b, 82c, 82d are still holding the clamp 60 open against the force of the urging members 66, 68. This allows precise positioning of the clamp 60 prior to deployment. The appendage 40 is shown beginning to cross the plane defined by the clamping portions 62, 64 of clamp 60, while the points at which the spreader legs 82a, 82b, 82c, 82d exert force against the clamping portions 62, 64 are shown to fall generally outside the boundaries of the appendage 40. This prevents direct contact between the spreader legs 82a, 82b, 82c, 82d and the appendage 40 during deployment or during post-deployment retrieval of the tool 80. Although FIGS. 8-10 show the lateral position of the legs 82a, 82b, 82c, 82d to be such that there is no direct contact between the spreader legs 82a, 82b, 82c, 82d and the appendage 40, as described above, the legs 82a, 82b, 82c, 82d may instead be placed laterally closer together if desired for any particular application.

Figure 11:
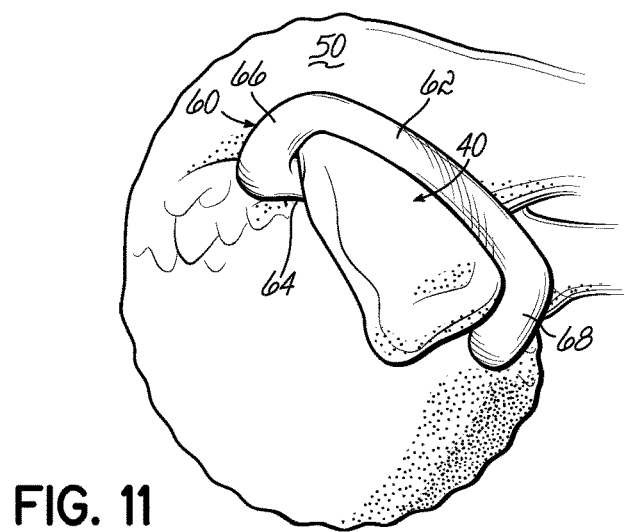
FIG. 11 shows the clamp of FIG. 5 having being deployed over an appendage.

FIG. 11 shows the tissue clamp 60 having been deployed on an appendage 40. The sutures 81a, 81b, 81c, 81d have been cut and spreader legs 82a, 82b, 82c, 82d have been removed from the clamp 60, allowing the full force applied by the urging members 66, 68 to be applied against the appendage 40 by the closing bias of the clamping portions 62, 64 of the clamp 60. As FIG. 11 shows, the deployed position of the clamp 60 is such that the urging members 66, 68 extending from the plane defined by the clamping portions 62, 64 face away from the heart 50, so as to minimize unnecessary or undesirable contact of the urging members with the heart 50. Any other orientation or configuration of urging members 66, 68 may be chosen as desired or necessary.

Alternate embodiments show ways to add length to the urging members 66, 68 in order to reduce the overall stress and thus prevent elastic yield of the material. Uses of superelastic material such as nickel titanium alloys are preferred and shown in previous embodiments, not only for its resistance to yielding but also for its biocompatibility. However, it is also possible to use other materials such as a spring-type biocompatible steel. Without departing from the scope of this invention, alternate materials such as plastics, elastomers and metals can be used in the construction of urging members 66, 68 and other portions or components of the various clamps disclosed herein.

Figure 12:
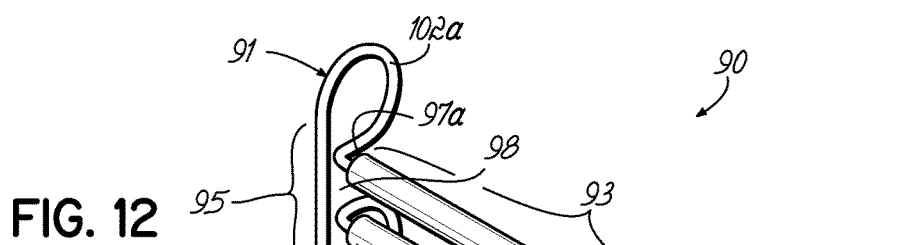
FIG. 12 shows an alternate embodiment of a clamp in which the urging members are closer to the ends of the rigid tubular members.

FIG. 12 shows an alternate embodiment of a clamp 90 whereby the urging members 91, 92 are in close proximity to the ends 97a, 97b, 97c, 97d of the rigid clamping portions 93, 94. Portions 95, 96 of the urging members 91, 92 serve to block the sides of the anatomical structure (e.g., appendage 40) being treated from entering the urging member areas 98, 99 and potentially resulting in portions of the appendage 40 or other structure being left unclamped. The embodiment of FIG. 12 shows urging members 91, 92 formed with wire on planes parallel to each other and generally perpendicular or at least transverse at some angle to the clamping portions 93, 94 of the clamp 90 in a manner similar to that of clamp 10 of FIGS. 1A-1D. The urging members 91, 92 of this alternate embodiment, however, are each shaped with a double loop. Specifically, straight segments 95, 96 of urging members 91, 92 are perpendicular to the axes of the clamping portions 93, 94. The ends of the straight segments 95, 96 connect to looped portions of wire 102a, 102b, 102c, 102d. The additional length of wire will assist with reducing overall stress on the wire.

Figure 13:
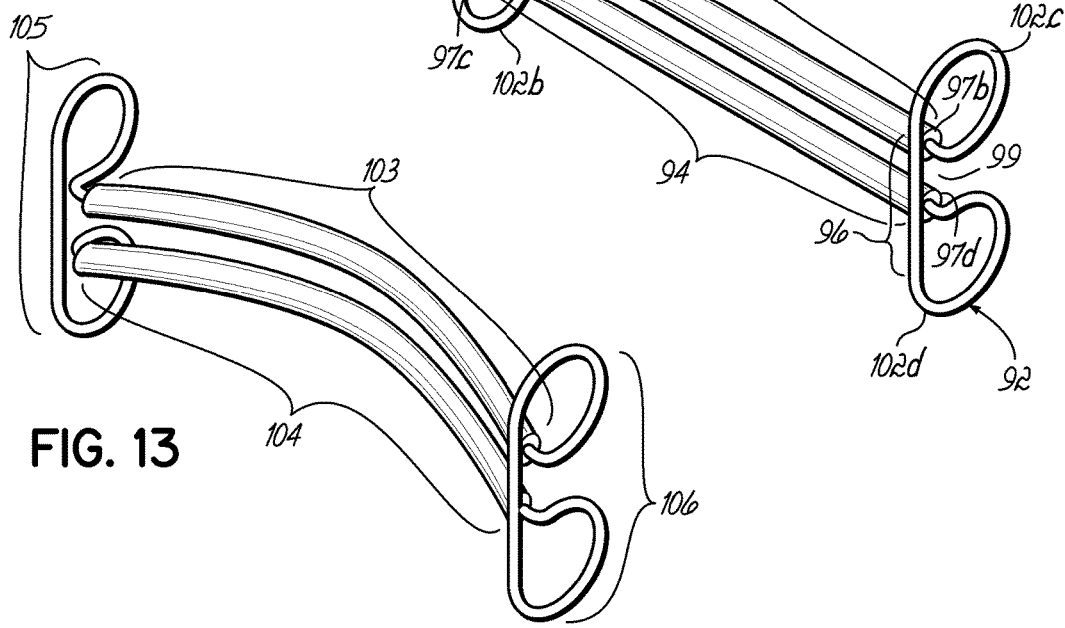
FIG. 13 shows an alternate embodiment of a clamp in which the clamping portions are bent to better match anatomy.
Figure 14:
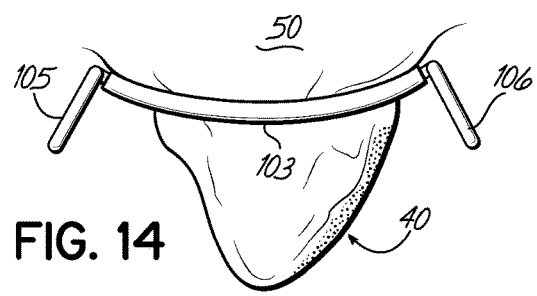
FIG. 14 shows a top view of the clamp of FIG. 13.

FIGS. 13 and 14 show an embodiment of a clamp 100 similar to clamp 90 of FIG. 12, however, the shape has been generally adapted to more closely match the anatomy surrounding the appendage 40 or other anatomical structure being treated. In this particular embodiment, the rigid clamping portions 103, 104 are curved such that, while extending generally perpendicular to planes that contain urging members 105, 106, they will generally follow the convex curvature of the outer wall of the heart 50 or other organ or tissue surrounding the anatomical structure being treated. Another advantage of this embodiment is the ability to clamp the anatomical structure (e.g., appendage 40) at different cross-sectional planes, which may be desirable in cases where the thickness of the appendage 40 or similar structure is very irregular, making the clamping profile of this embodiment more desirable than the single cross-sectional plane clamping enabled by the clamp 10 of FIGS. 1A-1D for example.

Figure 15:
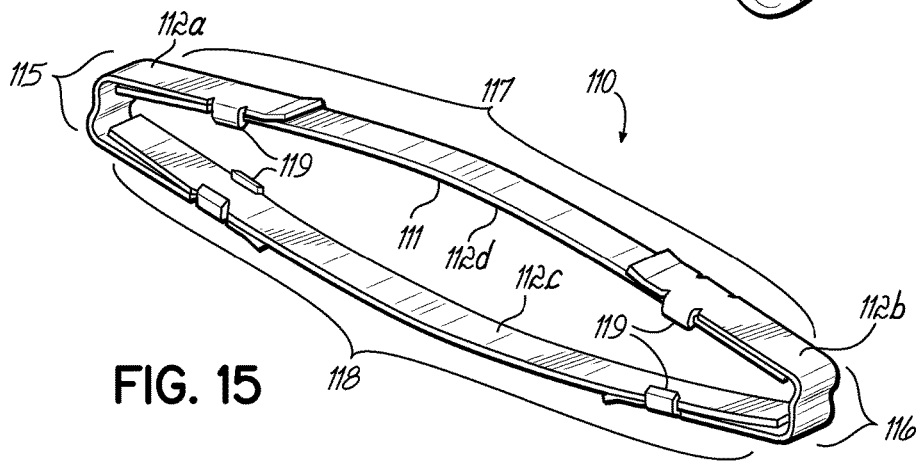
FIG. 15 shows an alternate embodiment of a clamp in which the urging members and clamping portions are formed from a flat spring material.

FIG. 15 is yet another embodiment of a clamp 110 in which the urging members 115, 116 and the rigid members 117, 118 are made of a flat spring material 111 having a generally rectangular cross-section. The construction shown in FIG. 15 is formed by four separate segments 112a, 112b, 112c, 112d of this flat material 111, consisting of two urging members 115, 116 and two clamping portions 117, 118. The urging members 115, 116 follow a generally C-shape profile, the ends of which overlap the ends of the clamping portions 117, 118. Side clips 119 extend from the urging members 115, 116 and around the flat rigid clamping portions 117, 118 to fix the parts together, frictionally preventing sliding of the urging members 115, 116 with respect to the clamping portions 117, 118. The flat clamping portions 117, 118 may be rigid or semi-rigid and can be made of various metallic or nonmetallic materials, or both. A suitable nonmetallic material would be a plastic such as a polycarbonate. A benefit of this type of flat construction lies in the ability to avoid the addition of any load-spreading surface such as the platens 67, 69 of FIG. 4, since the clamping portions 117, 118 already have a relatively larger area of contact with the anatomical structure to be treated. The flat shape of the urging members 115, 116 as compared to the wire construction of the clamp 10 of FIGS. 1A-1Dsimilarly results in less point-loading on the clamped tissue or organ or surrounding tissue. The ease of assembly of the embodiment of clamp 110 can be appreciated as yet another benefit, as the need for the steps of locating and swaging of rigid tubular members 63, 65 over a wire member 72 is eliminated. The ability to cut the flat clamping portions 117, 118 to a desired length to accommodate for smaller anatomical structures and the ease of clip-based assembly regardless of such desired length of the clamping portions 117, 118, is also an advantage of this embodiment.

FIG. 16 illustrates a clamp 120 in accordance with another embodiment. The construction of this embodiment is similar to that of FIG. 12, but the wire forming urging members 121, 122 includes two additional rectilinear segments as compared to the embodiment of FIG. 12. Thus, urging members 121, 122 each have respective first loop sections 128a, 128b, followed by rectilinear segments 125a, 125b perpendicular to the clamping portions 123, 124. Second rectilinear segments 126a, 126b are formed parallel to the first segments 125a, 125b. Third rectilinear segments 127a, 127b are located immediately adjacent to and on the same plane as the first rectilinear segments 125a, 125b, followed by second loop segments 129a, 129b. As in the construction of the embodiment of FIG. 12, the loop sections 128a, 128b, 129a, 129b of the urging members 121, 122 in this embodiment end at the point where they connect to each of the two clamping portions 123, 124. The result of this profile for urging members 121, 122 is the formation of a spring capable of exerting a higher bias force than do the urging members 91, 92 of FIG. 12. Like an axial spring, the respective ends 131a, 131b, 132a, 132b of the urging members 121, 122 are connected to the clamping portions 123, 124 and thus impart a closing force on clamping portions 123, 124. The advantages of this embodiment are the same as those described above for the embodiment of FIG. 12, but with the added benefits that the clamping force exerted on the treated anatomical structure may be of a greater magnitude and lower internal stress may be generated in the urging members 121, 122.

FIG. 17 shows another embodiment of a clamp 130 in which the ends 133, 134, 135, 136 of each of the clamping portions 131, 132 crosses over the adjacent end of the opposite clamping portion, resulting in non-parallel clamping portions 131, 132. An advantage of this embodiment is the ability to prevent portions of the anatomical structure being treated from entering the urging areas 139, 141 of the clamp 130.

FIG. 18 shows a clamp 140 similar to that of FIG. 15 but with greater space between the rigid members 148, 149 at the ends near the urging members 141, 142. This configuration may be more advantageous for thicker tissue such as a bowel. This embodiment primarily differs from that of FIG. 15 in that the middle section 143 of the C-shape of the urging member 141, 142 profile has been enlarged.

Figure 19:
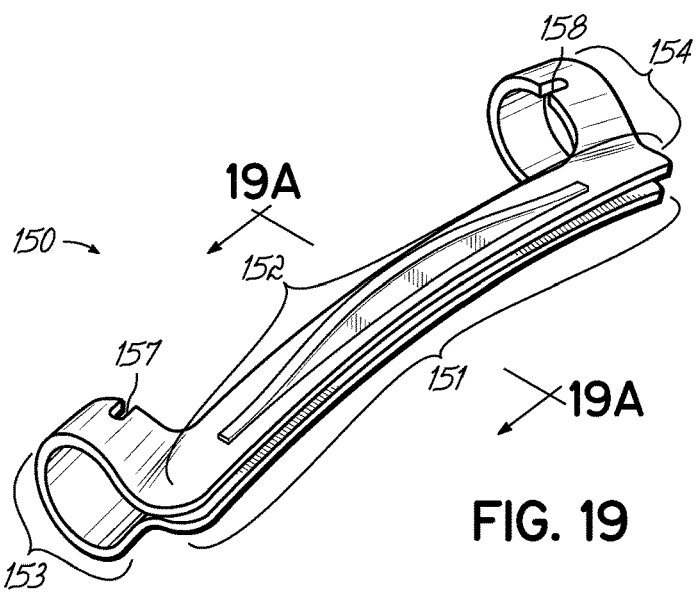
FIG. 19 shows an alternate embodiment of a clamp in which the clamping portions and urging members are made of the same starting stock of material.
Figure 19A:
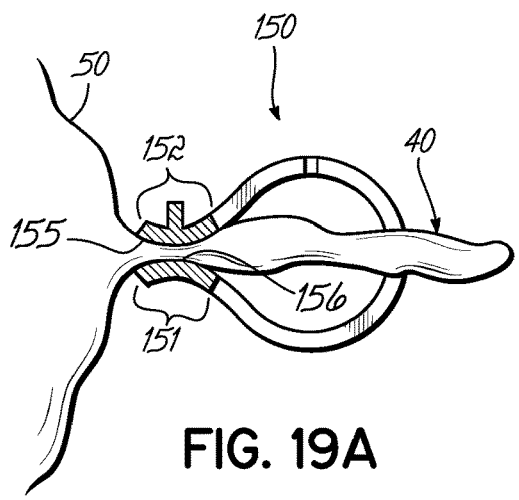
FIG. 19A is a cross-sectional view of the clamp of FIG. 19, showing the clamp in its deployed position around an anatomical structure.

FIGS. 19 and 19A show an alternate embodiment of a clamp 150 in which the clamping portions 151, 152 and urging members 153, 154 are made from the same basic substrate material and from the same starting stock of such material, preferably one approximating a tube. The substrate could either be a plastic or metal. This configuration would be especially suited for a bio-absorbable material. This material could be coated with the same polyester as in the velour fabric noted earlier to enhance tissue ingrowth and stability of the clamp 150 until the anatomical structure has atrophied. Additionally, textures or porosity on the tissue gripping surfaces 155, 156 may increase friction and adhesion to the clamped tissue until ingrowth and stability have been achieved. The construction of this embodiment 150 consists of two flat clamping portions 151, 152 joined at the ends by urging members 153, 154 following a loop profile and with such urging members 153, 154 each including a notch 157, 158 to facilitate deployment or application to tissue with a suitable tool (not shown).

Figure 20:
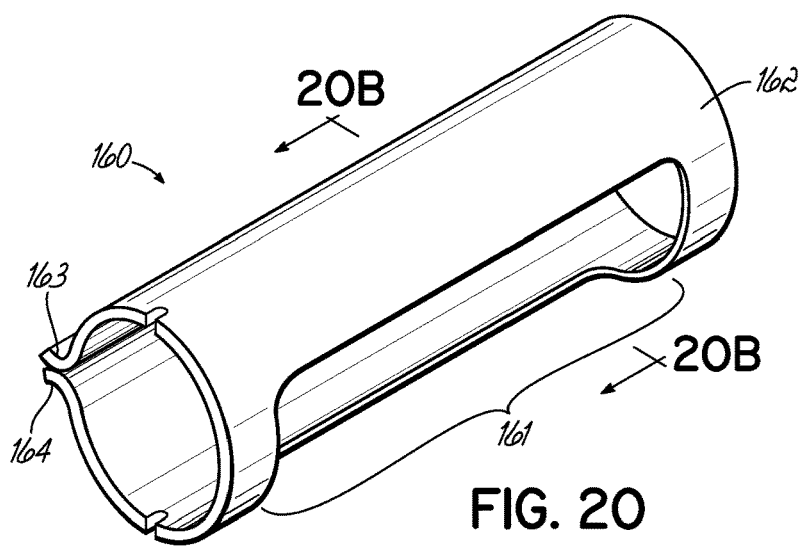
FIG. 20 is an alternate embodiment of the clamp of FIGS. 19 and 19A made from a tube or roll of sheet metal.
Figure 20A:
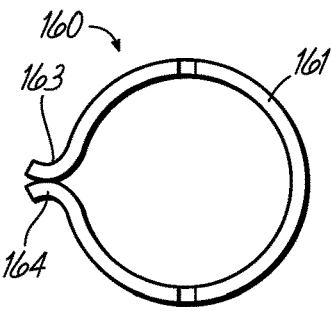
FIG. 20A is a cross-sectional view of the clamp of FIG. 20 in its closed, pre-deployment position.
Figure 20B:
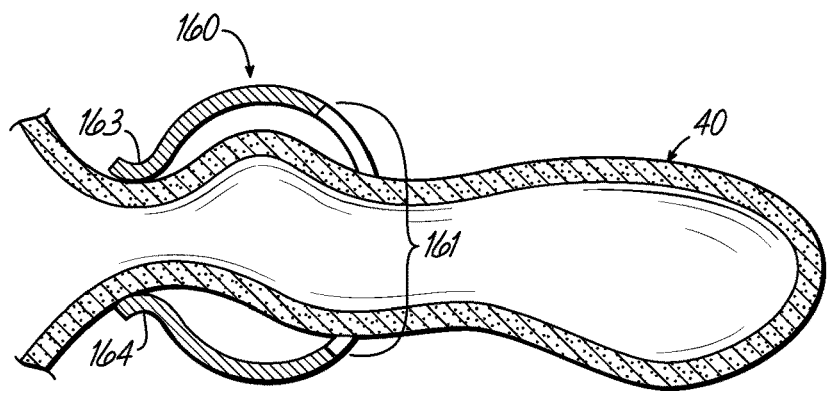
FIG. 20B is a cross-sectional view of the clamp of FIGS. 20 and 20A in its deployed position.

FIGS. 20, 20A and 20B show a slight variation of the embodiment of FIGS. 19 and 19A, depicting a different manufacturing method. This clamp 160 is made from a tube or roll formed from sheet-metal. Lower cost manufacturing methods such as roll forming and metal piercing may be more advantageous to reduce the cost of goods versus a multiple step assembly such as that shown in other embodiments. Of course, such benefits must be weighed against any perceived advantages of the more costly designs in use. Thus, this embodiment consists of the removal of part of the surface of a tube or roll 162, with the material thus removed forming the clamp opening 161. A longitudinal split of the tube is then formed into flat members 163, 164 constituting the clamping portions of this embodiment.

Figure 21:
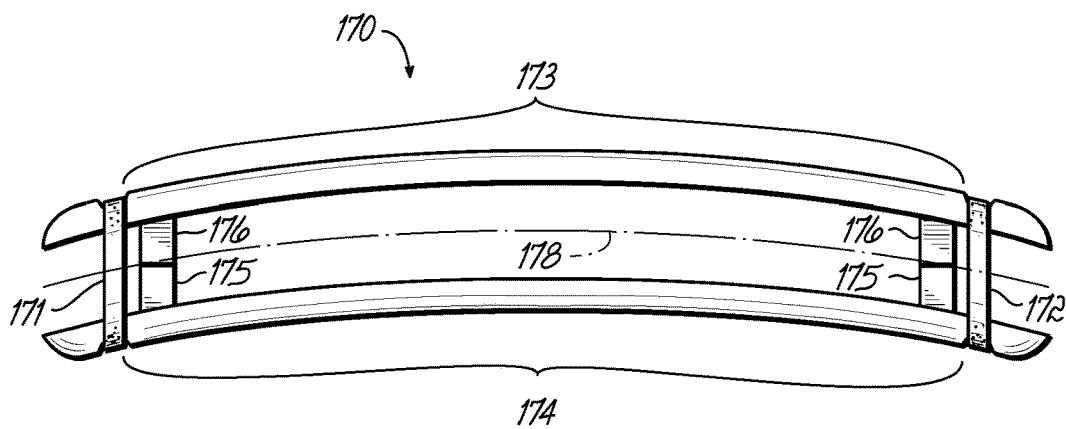
FIG. 21 is a side view of an alternate embodiment of a clamp, in which the urging members are made from elastic bands.
Figure 22:
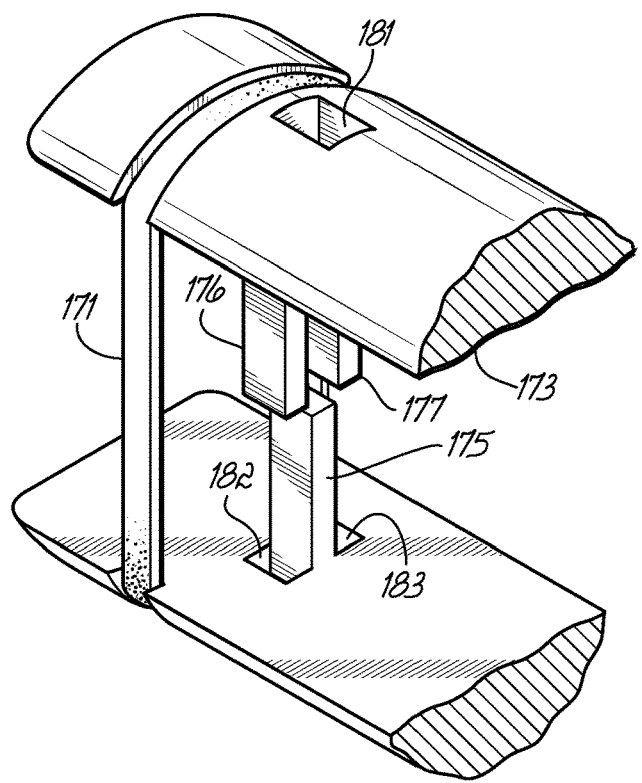
FIG. 22 is a perspective view of the clamp of FIG. 21, showing tissue-blocking fingers protruding from each clamping portion and with corresponding receiving apertures.

FIGS. 21 and 22 show another embodiment whereby the urging members 171, 172 between the two rigid clamping portions 173, 174 are bands of elastic material. The elastic bands 171, 172 connect the two clamping portions 173, 174. In addition, tissue blocking or damming fingers 175-177 extend from either rigid clamping portions 173, 174 towards the center 178 between the two clamping portions 173, 174, thereby preventing tissue from becoming entangled in the elastic urging members. 171, 172. These fingers 175-177 furthermore engage each of the opposite clamping portions 173, 174 by entering into apertures 181-183 adapted for that purpose. Biocompatible urging members 171, 172 such as silicone elastomer could be used in this configuration. In addition, the rigid members 173, 174 could easily be made from an absorbable polymer. Still further, the assembly could be covered in a polyester velour fabric 74 (FIG. 5) to promote tissue ingrowth and stability until the anatomical structure has had a chance to atrophy.

Figure 23:
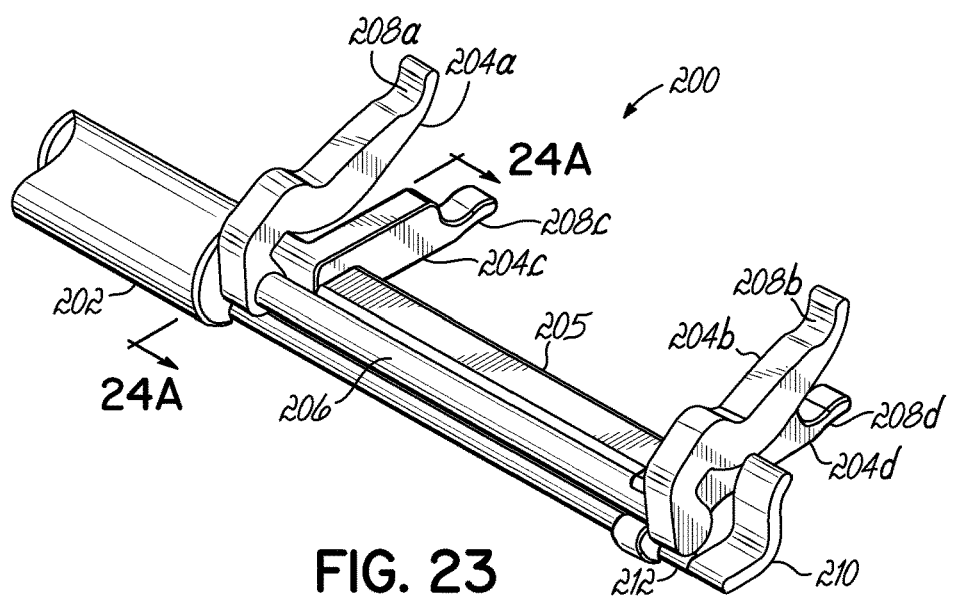
FIG. 23 is a perspective view of the distal end of an endoscopic tool useful for applying a clamp in accordance with the invention.
Figure 24A:
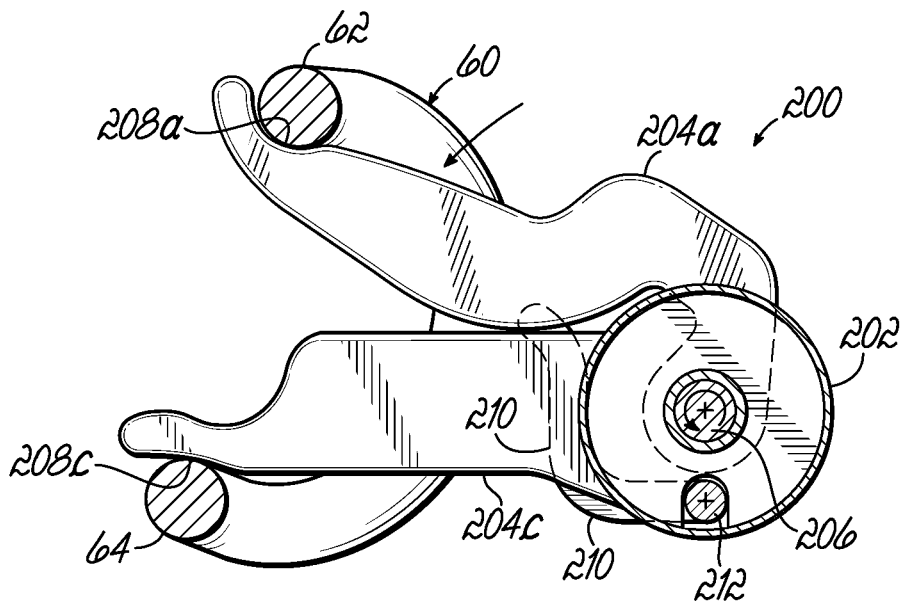
FIG. 24A is cross sectional view of FIG. 23 taken along line 24A-24A of FIG. 23.
Figure 24B:
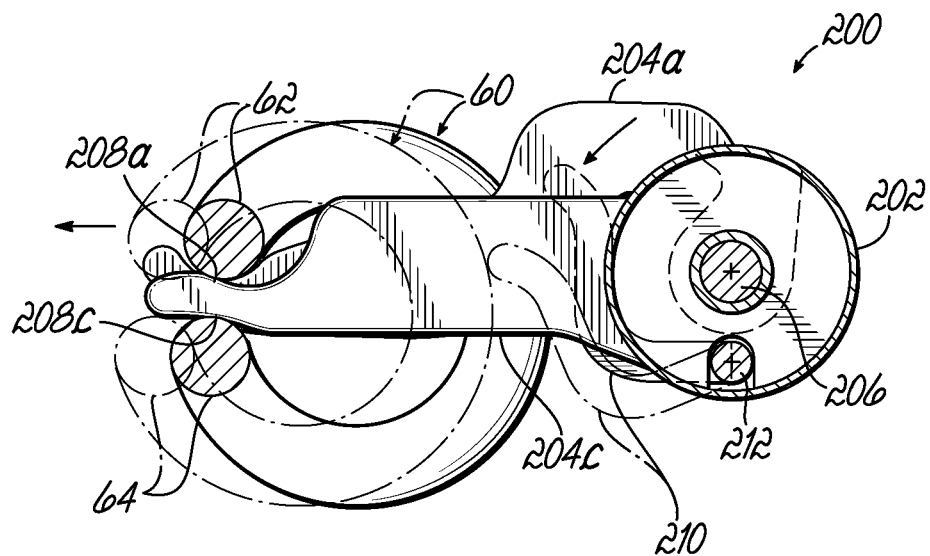
FIG. 24B is a cross sectional view similar to FIG. 24A, but illustrating the tool in a closed or clamping position.

FIGS. 23, 24A and 24B illustrate an alternative tool 200 to those discussed in FIGS. 6, 6A, and 6B. While the tools discussed in FIGS. 6, 6A and 6B may be used most easily in open surgical methods, it would be desirable to provide systems better suited for less invasive procedures, such as endoscopic procedures. The tool 200 shown in FIGS. 23, 24A and 24B is one example of a tool useful in such less invasive procedures and comprises an elongate member 202 shown broken away, but which may be formed with any suitable length for access purposes through a port in the body of a patient (e.g., subxiphoid, intercostal space, etc.). One set of legs 204a, 204b may be rigidly fixed to the elongate member 202 and/or to other suitable rigid structure 205 either associated with the elongate member 202 or extending within the elongate member 202. Another set of legs 204c, 204d is coupled to a rotatable shaft 206 extending within the elongate member 202. The rotatable shaft or actuating member 206 may be rotated through the use of a suitable handle or knob (not shown), for example, located at a proximal end of the tool 200 outside the body of the patient, when in use. The legs 204a, 204b, 204c, 204d have respective recesses 208a, 208b, 208c, 208d configured to receive the clamping portions 62, 64 generally as previously described. When the pair of legs is rotated by rotation of the shaft 206, this will spread the clamping portions 62, 64 apart as shown in FIG. 24A. Rotation of the shaft 206 in the opposite direction will allow the normally closed clamping portions 62, 64 to naturally come together against opposite sides of the desired tissue (not shown). The tool 212 further includes one or more clamp removal members 210 coupled to another rotatable shaft 212 that may also be coupled to a proximally located handle or knob (not shown). When this shaft 212 is rotated after the clamp 60 has been applied as shown in FIG. 24B, the clamp 60 will be urged or pushed away from the legs 204a, 204b, 204c, 204d as shown in comparing the solid line depictions to the dash-dot line depictions in FIG. 24B. It will be appreciated that multiple clamp removal members may be provided for contact along the length of the clamp 60 such that a more uniform removal force is applied along the length of the clamp 60.

While the present invention has been illustrated by a description of various preferred embodiments and while these embodiments have been described in some detail, it is not the intention of the Applicant to restrict or in any way limit the scope of the appended claims to such detail. Additional advantages and modifications will readily appear to those skilled in the art. The various features of the invention may be used alone or in any and all combinations depending on the needs and preferences of the user. This has been a description of the present invention, along with the preferred methods of practicing the present invention as currently known.

What is claimed is:

1. A device for occluding a left atrial appendage of the heart, the device comprising:
   first and second elongate clamping elements configured to be placed on opposite, outside surfaces of the left atrial appendage, and
   first and second resilient urging members coupled with the first and second elongate clamping elements to form an assembly, the first and second resilient urging members configured to urge at least one of said first and second elongate clamping elements toward the other of said first and second elongate clamping elements from an open position into a clamping position to occlude the appendage, the first and second resilient urging members being generally C-shaped with respective legs of each generally C-shaped urging member overlapping the first and second elongate clamping elements,
   the assembly configured to receive the appendage in the open position and occlude the hollow interior of the appendage in the clamping position,
   wherein the first and second elongate clamping elements have tissue engaging surfaces for engaging the appendage in the clamping position and promoting tissue ingrowth.

2. The device of claim 1, wherein each of the first and second resilient urging members includes a pair of receiving portions, and each of the elongate clamping elements includes a pair of projecting portions, each of the receiving portions receiving a projecting portion of one of the first or second elongate clamping elements.

3. The device of claim 2, wherein the receiving portions and projecting portions are rounded.

4. The device of claim 1, wherein said first and second resilient urging members normally spring bias at least one of said first and second elongate clamping portions toward the other of said first and second elongate clamping portions when said first and second elongate clamping portions are in the open position.

5. The device of claim 1, wherein each of the first and second elongate clamping elements includes first and second ends, and the legs of the first generally C-shaped urging member overlap the first ends of the first and second elongate clamping elements and the legs of the second generally C-shaped urging member overlap the second ends of the first and second elongate clamping elements.

6. The device of claim 1, wherein the first and second elongate clamping elements are formed of nonmetallic material.

7. The device of claim 1, wherein the tissue engaging surfaces each comprise a surgical grade fabric.

8. A device for occluding a left atrial appendage of the heart, the device comprising:
   first and second elongate clamping elements configured to be placed on opposite, outside surfaces of the left atrial appendage, and
   first and second resilient urging members coupled with the first and second elongate clamping elements to form an assembly, the first and second resilient urging members configured to urge at least one of said first and second elongate clamping elements toward the other of said first and second elongate clamping elements from an open position into a clamping position to occlude the appendage, the first and second resilient urging members being generally C-shaped,
   wherein each of the first and second elongate clamping elements includes first and second ends, and the legs of the first generally C-shaped urging member overlap the first ends of the first and second elongate clamping elements,
   the assembly configured to receive the appendage in the open position and occlude the hollow interior of the appendage in the clamping position,
   wherein the first and second elongate clamping elements have tissue engaging surfaces for engaging the appendage in the clamping position and promoting tissue ingrowth.

9. The device of claim 8, wherein each of the first and second resilient urging members includes a pair of receiving portions, and each of the elongate clamping elements includes a pair of projecting portions, each of the receiving portions receiving a projecting portion of one of the first or second elongate clamping elements.

10. The device of claim 9, wherein the receiving portions and projecting portions are rounded.

11. The device of claim 8, wherein said first and second resilient urging members normally spring bias at least one of said first and second elongate clamping portions toward the other of said first and second elongate clamping portions when said first and second elongate clamping portions are in the open position.

12. The device of claim 8, wherein the first and second elongate clamping elements are formed of nonmetallic material.

13. The device of claim 8, wherein the tissue engaging surfaces each comprise a surgical grade fabric.

* * * * *